United States Patent
van der Walt et al.

(10) Patent No.: US 7,381,208 B2
(45) Date of Patent: Jun. 3, 2008

(54) CRYOSURGICAL DEVICES FOR ENDOMETRIAL ABLATION

(75) Inventors: Nicholas R. van der Walt, Hillcrest Park (ZA); Jia Hua Xiao, Maple Grove, MN (US); David W. Vancelette, St. Louis Park, MN (US)

(73) Assignee: AMS Research Corporation, Minnetonka, MN (US)

(*) Notice: Subject to any disclaimer, the term of this patent is extended or adjusted under 35 U.S.C. 154(b) by 515 days.

(21) Appl. No.: 11/020,792

(22) Filed: Dec. 22, 2004

(65) Prior Publication Data

US 2005/0177148 A1 Aug. 11, 2005

Related U.S. Application Data

(60) Provisional application No. 60/546,334, filed on Feb. 20, 2004, provisional application No. 60/532,420, filed on Dec. 22, 2003, provisional application No. 60/532,419, filed on Dec. 22, 2003.

(51) Int. Cl.
*A61B 18/18* (2006.01)
(52) U.S. Cl. .......................................... 606/21; 606/23
(58) Field of Classification Search ............. 606/20–26
See application file for complete search history.

(56) References Cited

U.S. PATENT DOCUMENTS

| | | | |
|---|---|---|---|
| 3,369,549 A * | 2/1968 | Armao | .................. 606/21 |
| 3,613,689 A | 10/1971 | Crump et al. | |
| 3,924,628 A | 12/1975 | Droegemueller et al. | |
| 4,602,174 A | 7/1986 | Redlich | |
| 5,211,646 A * | 5/1993 | Alperovich et al. | .......... 606/23 |
| 5,275,595 A | 1/1994 | Dobak, III | |
| 5,334,181 A | 8/1994 | Rubinsky et al. | |
| 5,403,309 A | 4/1995 | Coleman et al. | |
| 5,449,380 A * | 9/1995 | Chin | ...................... 607/105 |

(Continued)

FOREIGN PATENT DOCUMENTS

WO    WO 02/04042    1/2002

(Continued)

OTHER PUBLICATIONS

J. Jones, "Mixed Gas Sorption Joule-Thomson Refrigerator," NASA Tech Briefs, vol. 15(5) May 1991, pp. 38 and 40.

(Continued)

*Primary Examiner*—Michael Peffley
(74) *Attorney, Agent, or Firm*—Kimberly K. Baxter

(57) ABSTRACT

A cryoablation system for performing endometrial ablation comprising an elongated tubular cannula having a proximal end, a distal end, and a longitudinal axis, an expandable balloon extending from the distal end of the cannula and fluidly connected to a source of heat transfer fluid by at least one fluid path, a pump for circulating the heat transfer fluid into and out of the balloon, a probe handle coupled to the proximal end of the cannula and in fluidic communication with the balloon through the cannula, and a heat exchanger for varying the temperature of the heat transfer fluid, wherein the heat exchanger is fluidly connected to a secondary refrigerant source, and wherein the heat exchanger comprises an outer tubular wall and a plurality of fins extending from the tubular wall toward the interior portion of the heat exchanger.

14 Claims, 6 Drawing Sheets

U.S. PATENT DOCUMENTS

| | | | |
|---|---|---|---|
| 5,501,681 A * | 3/1996 | Neuwirth et al. ............. 606/21 |
| 5,522,870 A | 6/1996 | Ben-Zion |
| 5,525,845 A | 6/1996 | Beale et al. |
| 5,592,073 A | 1/1997 | Redlich |
| 5,595,065 A | 1/1997 | Boiarski et al. |
| 5,603,221 A | 2/1997 | Maytal |
| 5,617,739 A | 4/1997 | Little |
| 5,642,088 A | 6/1997 | Unger |
| 5,644,502 A | 7/1997 | Little |
| 5,647,868 A | 7/1997 | Chinn |
| 5,674,218 A | 10/1997 | Rubinsky et al. |
| 5,702,435 A | 12/1997 | Maytal |
| 5,716,353 A | 2/1998 | Matsuura et al. |
| 5,724,832 A | 3/1998 | Little et al. |
| 5,741,248 A | 4/1998 | Stern et al. |
| 5,758,505 A * | 6/1998 | Dobak et al. ..................... 62/6 |
| 5,759,182 A * | 6/1998 | Varney et al. ................. 606/21 |
| 5,787,715 A | 8/1998 | Dobak, III et al. |
| 5,891,188 A | 4/1999 | Maytal |
| 5,901,783 A | 5/1999 | Dobak, III et al. |
| 5,910,104 A | 6/1999 | Dobak, III et al. |
| 5,954,714 A | 9/1999 | Saadat et al. |
| 5,956,958 A | 9/1999 | Dobak, III et al. |
| 6,035,657 A | 3/2000 | Dobak, III et al. |
| 6,074,572 A | 6/2000 | Li et al. |
| 6,151,901 A | 11/2000 | Dobak, III et al. |
| 6,182,666 B1 * | 2/2001 | Dobak ........................ 128/898 |
| 6,193,644 B1 | 2/2001 | Dobak, III et al. |
| 6,237,355 B1 | 5/2001 | Li |
| 6,241,722 B1 | 6/2001 | Dobak et al. |
| 6,270,494 B1 | 8/2001 | Kovalcheck et al. |
| 6,306,129 B1 | 10/2001 | Little et al. |
| 6,379,348 B1 | 4/2002 | Onik |
| 6,451,012 B2 | 9/2002 | Dobak, III |
| 6,471,217 B1 | 10/2002 | Hayfield et al. |
| 6,471,694 B1 | 10/2002 | Kudaravalli et al. |
| 6,475,212 B2 | 11/2002 | Dobak, III et al. |
| 6,505,629 B1 | 1/2003 | Mikus et al. |
| 6,530,234 B1 | 3/2003 | Dobak, III et al. |
| 6,537,271 B1 | 3/2003 | Murray et al. |
| 6,547,784 B1 | 4/2003 | Thompson et al. |
| 6,569,161 B2 | 5/2003 | Zappala |
| 6,607,545 B2 | 8/2003 | Kammerer et al. |
| 6,708,056 B2 | 3/2004 | Duchon et al. |
| 6,709,431 B2 | 3/2004 | Lafontaine |
| 2001/0016764 A1 | 8/2001 | Dobak, III |
| 2002/0193854 A1 | 12/2002 | Dobak, III et al. |
| 2003/0199732 A1 | 10/2003 | Suslian et al. |
| 2004/0002664 A1 | 1/2004 | Brookner et al. |
| 2004/0002698 A1 | 1/2004 | Hua Xiao et al. |
| 2004/0002702 A1 | 1/2004 | Xiao et al. |
| 2004/0002703 A1 | 1/2004 | Xiao et al. |
| 2004/0002747 A1 | 1/2004 | Ryan et al. |
| 2004/0002748 A1 | 1/2004 | Ryan et al. |
| 2004/0044334 A1 | 3/2004 | LaFontaine |
| 2004/0049176 A1 | 3/2004 | Lafontaine |
| 2004/0260328 A1 * | 12/2004 | Zvuloni et al. ............. 606/194 |

FOREIGN PATENT DOCUMENTS

| WO | WO 03/026719 | 4/2003 |
|---|---|---|

OTHER PUBLICATIONS

O. Istre et al., "Oral Presentations," Journal of the American Association of Gynecologic Laparascopists, vol. 10, No. 3 Supplement, Aug. 2003, pp. S1, S12, and S13.

R. Pittrof et al., "Endometrial cryoblation using 0.9% saline as a uterine distension medium: a feasibility study," Minimally Invasive Therapy 1992: 1: pp. 283-286.

Cyril Young et al., "Out-Patient Cervical Cryosurgery," The Journal of Obstetrics and Gynecology of the British Commonwealth, vol. 79, Aug. 1972, pp. 753-755.

* cited by examiner

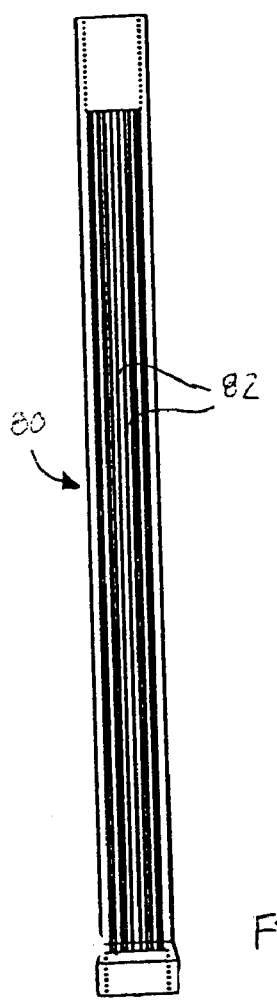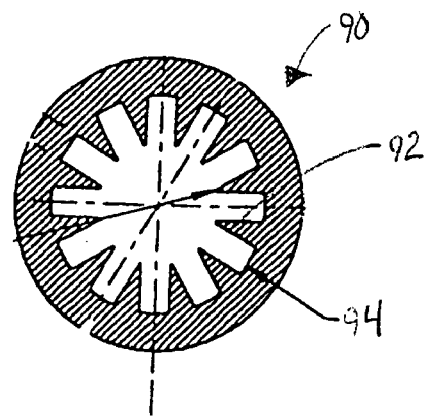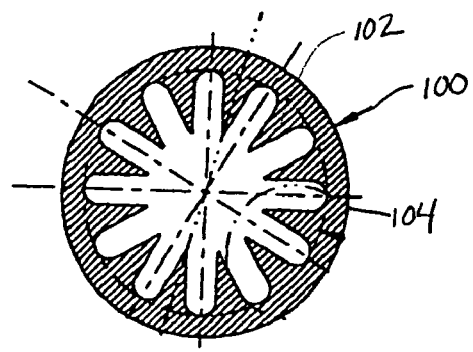
Fig. 5
Fig. 6
Fig. 7

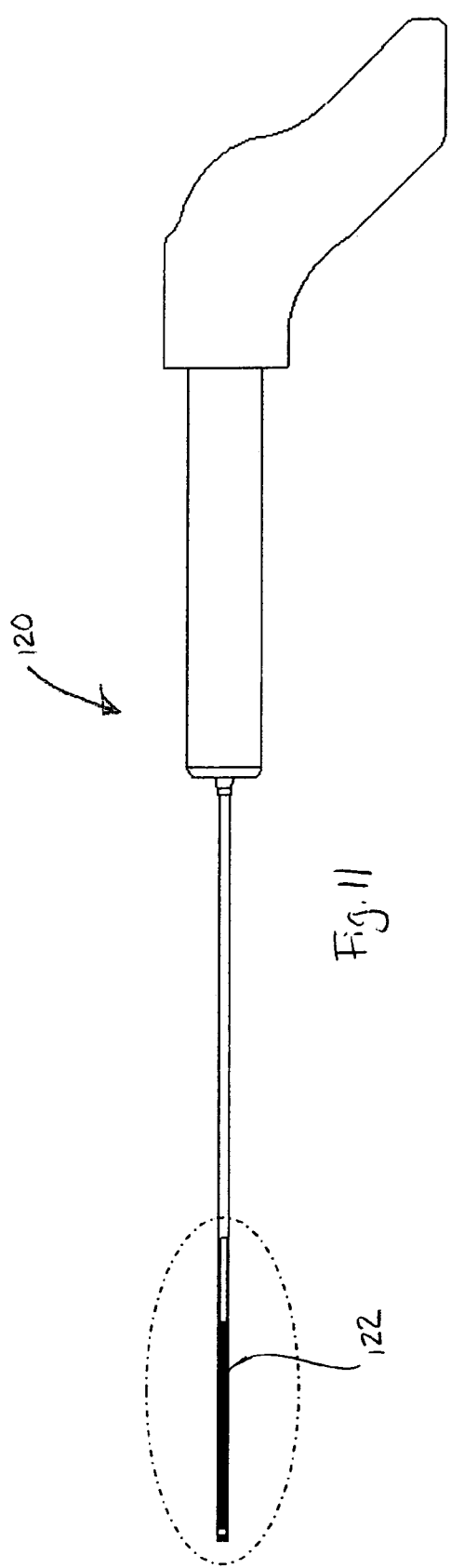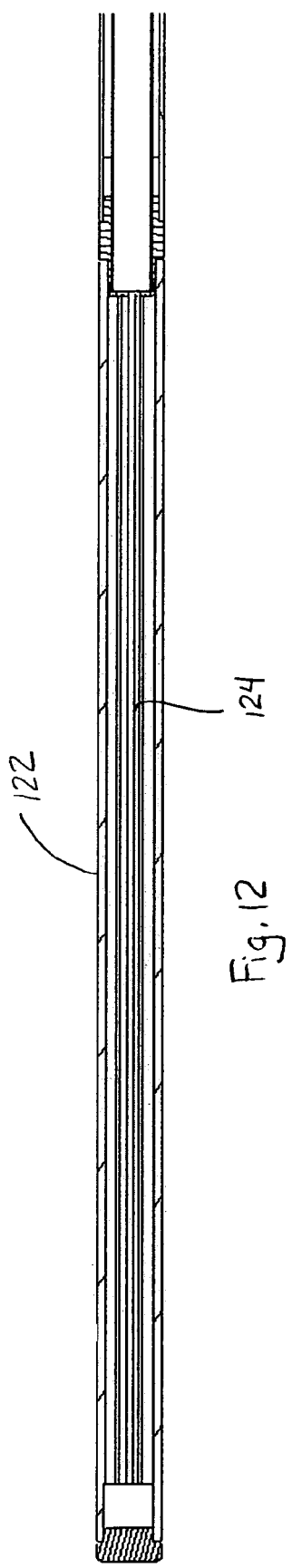

CRYOSURGICAL DEVICES FOR ENDOMETRIAL ABLATION

REFERENCE TO RELATED APPLICATIONS

This application claims the benefit of U.S. Provisional applications having Ser. No. 60/532,420, filed Dec. 22, 2003, entitled "DEVICE FOR TREATING ENDOMETRIAL ABLATION"; Ser. No. 60/532,419, filed Dec. 22, 2003, entitled "EXPANDABLE MEMBER WITH CIRCULATING CHILLED LIQUID FOR GLOBAL ENDOMETRIAL ABLATION"; and Ser. No. 60/546,334, filed Feb. 20, 2004, entitled "CRYOSURGICAL DEVICES FOR ENDOMETRIAL ABLATION", which applications are incorporated herein by reference in their entireties.

TECHNICAL FIELD

The present invention relates generally to cryosurgical devices for freezing and destroying biological tissues. More specifically, the invention relates to cryosurgical devices that can be used for freezing and thereby destroying endometrial tissues within the uterus of a female patient.

BACKGROUND OF THE INVENTION

Endometrial ablation is a common surgical procedure that is used to treat menorrhagia in women, which is typically accomplished through the application of either sufficiently hot or sufficiently cold temperatures to destroy the lining of the uterus. One type of procedure used for endometrial ablation involves the use of a device that rolls over the surface of the uterine wall while applying enough heat to destroy the endometrial tissue. While this type of procedure can be effective, it requires a significant amount of time and skill in anipulating the rolling device to ensure that the entire endometrium is destroyed.

Another type of procedure used for endometrial ablation also uses heat, but instead involves balloons or similar distensible bladders. These balloons are inserted into the uterus and inflated with a fluid until the balloon contacts the affected surfaces of the uterus. Fluid is then heated to an appropriate temperature to ablate or destroy the endometrium. Good surface contact is important to get complete coverage of the uterine lining. However, such coverage can be difficult due to temperature fluctuations and gradients along the surface of the balloon that can be caused by any factors, such as convective currents of the fluid within the balloon. To improve control of the fluid temperature within the balloon, various mechanical devices and systems have been used for circulating or agitating the heated fluid, such as through multiple fluid passageways, propellers within a lumen contained within the balloon, vibrating members, and electrical impulses. These mechanical devices or systems provide varying degrees of effectiveness, depending on the administrator of the procedure and the device itself. In addition, the movement of hot fluid into the balloon can sometimes cause discomfort or possible tissue damage to the vagina and opening of the cervix as heat is conducted through the walls of the catheter to which the balloon is attached.

Another group of procedures used for endometrial ablation involves the application of extremely low temperatures and is commonly referred to as cryosurgery. In the performance of cryosurgery, it is typical to use a cryosurgical application system designed to suitably freeze the target tissue. The abnormal or target cells to be destroyed are often surrounded by healthy tissue that should be left uninjured. Many of these systems use a probe with a particular shape and size that is therefore designed to contact a selected portion of the tissue that is to be treated without undesirably affecting any adjacent tissue or organs. In one particular application used to treat conditions of abnormal uterine bleeding, cryoablation instruments and techniques are used to freeze endometrial tissue, thereby destroying at least a portion of the endometrium or lining of the uterus, while leaving the remainder of the uterus undamaged. An example of a device that can be used for this type of cryoablation is the Her Option Cryoablation System, commercially available from American Medical Systems of Minnetonka, Minn. In this type of system, a rigid probe is provided with a very cold tip that freezes the endometrial tissue with which it comes in contact. Where such a probe is used, the remainder of the refrigeration system must be designed to provide adequate cooling, which involves lowering the operative portion of the probe to a desired temperature and having sufficient power or capacity to maintain the desired temperature for a given heat load. The entire system must be designed so that the operative portion of the probe can be placed at the location of the tissue to be frozen without having any undesirable effect on other organs or systems. For this reason, probes in these types of systems are often in the shape of an elongated tube with a rounded tip area at one end that can be positioned within the uterus for the cryoablation procedures. Other cryocooling surgical devices, components thereof, and surgical methods are disclosed in U.S. Pat. Nos. 5,275,595; 5,758,505; 5,787,715; 5,901,783; 5,910,104; 5,956,958; 6,035,657; 6,074,572; 6,151,901; 6,182,666; 6,237,355; 6,241,722; 6,270,494; 6,451,012; 6,471,217; 6,471,694; 6,475,212; 6,530,234; and 6,537,271, each of which is incorporated by reference in its entirety.

In many cases, the cold portion of an instrument or device is provided through the use of a Joule-Thompson refrigeration system. These refrigeration systems generally operate through the expansion of a high-pressure gas through an expansion element that includes some sort of a flow restrictor. The restriction of flow ay be accomplished through the use of a small orifice, a narrow capillary tube, or some other sort of passage that is smaller than the supply source through which the high-pressure gas must move. Typically, the refrigeration system includes a source of high-pressure gas, a heat exchanger, an expansion element, a heat transfer element, and various tubes or conduits that allow movement of the gas from one component to another. The high-pressure gas passes through the heat exchanger to lower the gas temperature at least slightly, then the gas temperature is further lowered through the isenthalpic expansion of the gas as it passes through the expansion element. This expanded and cooled gas is exposed to the heat transfer element, where the gas can then absorb the heat that has been transferred from the environment.

In most systems, the cooling tip is designed or chosen to be small enough to easily be accurately positioned at the treatment area, which generally limits the technique to applying the cooling to a relatively small area with each placement of the probe. The entire process thus typically requires that the probe be positioned at least two or three times to ablate the entire target area, such as an entire uterine cavity. Each relocation of the probe requires repetition of the same cooling steps, which can be time consuming and requires multiple precise placements of the probe to guarantee that the entire area is adequately ablated.

With these cryosurgical techniques, it is typically desirable to insulate the shaft of a cryosurgical probe to prevent the unintentional freezing of tissue at locations along the length of the probe that may inadvertently or unavoidably come in contact with the probe shaft. One way these shafts are often insulated is to provide a vacuum space along the probe shaft. This method is sometimes ineffective because the level of the vacuum maintained in such a space can degrade over time due to the outgassing of etals, plastics, and braze joints. This outgassing can increase during sterilization procedures in which heat is applied to the probe. Thus, it is known to incorporate the insulation into a disposable sheath that can be disposed over a probe, as is described in U.S. Pat. No. 6,182,666 (Dobak III), for example, so that the disposable element is not subjected to repeated sterilization, but instead can be discarded without significant degradation of the insulation. This disposable sheath can be constructed of a thermally resistive material, such as a plastic, to inhibit heat transfer between the surrounding tissues and the probe that it covers.

There is, however, a need to provide a system and device for endometrial ablation using cryosurgical methods that improve the overall coverage of the endometrial surface for a range of uterine sizes and shapes while maintaining an appropriate depth of ablation. There is further a need for these systems and devices to be easily manipulated to the affected areas, while having the ability to quickly generate an appropriately sized cold area or ice ball within the uterus for ablation. In addition, these systems will desirably include an efficient heat exchanger that provides improved cooling power with a given amount of input energy.

SUMMARY OF THE INVENTION

The present invention provides systems of performing endometrial ablation using cryoablation techniques that include a heat exchanger that provides for efficient cooling of the fluid used for the processes. The heat exchanger is configured to be unobstructive to good fluid flow through the system while achieving a pressure drop within a certain range with a variety of fluids. The heat exchanger of the invention may be used in currently available systems, such as the Her Option Cryoablation System, commercially available from American Medical Systems of Minnetonka, Minn.

In one aspect of this invention, a cryoablation system for performing endometrial ablation is provided comprising an elongated tubular cannula having a proximal end, a distal end, and a longitudinal axis, an expandable balloon extending from the distal end of the cannula and fluidly connected to a source of heat transfer fluid by at least one fluid path, a pump for circulating the heat transfer fluid into and out of the balloon, a probe handle coupled to the proximal end of the cannula and in fluidic communication with the balloon through the cannula, and a heat exchanger for varying the temperature of the heat transfer fluid, wherein the heat exchanger is fluidly connected to a secondary refrigerant source, and wherein the heat exchanger comprises an outer tubular wall and a plurality of fins extending from the tubular wall toward the interior portion of the heat exchanger.

In another aspect of the invention, a cryoablation system is provided with a handle from which a cannula extends, a cooling tip at the distal end of the handle, and a heat exchanger, where the heat exchanger comprises an outer tubular wall and a plurality of fins extending from the tubular wall toward the interior portion of the heat exchanger.

BRIEF DESCRIPTION OF THE DRAWINGS

The present invention will be further explained with reference to the appended Figures, wherein like structure is referred to by like numerals throughout the several views, and wherein:

FIG. 5 is a cross-sectional side view of a heat exchanger including multiple fins, in accordance with the invention;

FIG. 6 is a cross-sectional top view of a heat exchanger having one exemplary arrangement of fins;

FIG. 7 is a cross-sectional top view of a heat exchanger of the present invention having another arrangement of fins;

FIG. 11 is a front schematic view of a cryosurgical probe of the invention, including a finned heat exchanger at the distal end of the cannula; and FIG. 12 is an enlarged cross-sectional view of the circled portion of the probe of FIG. 11.

DETAILED DESCRIPTION OF THE PREFERRED EMBODIMENTS

Figure 1:
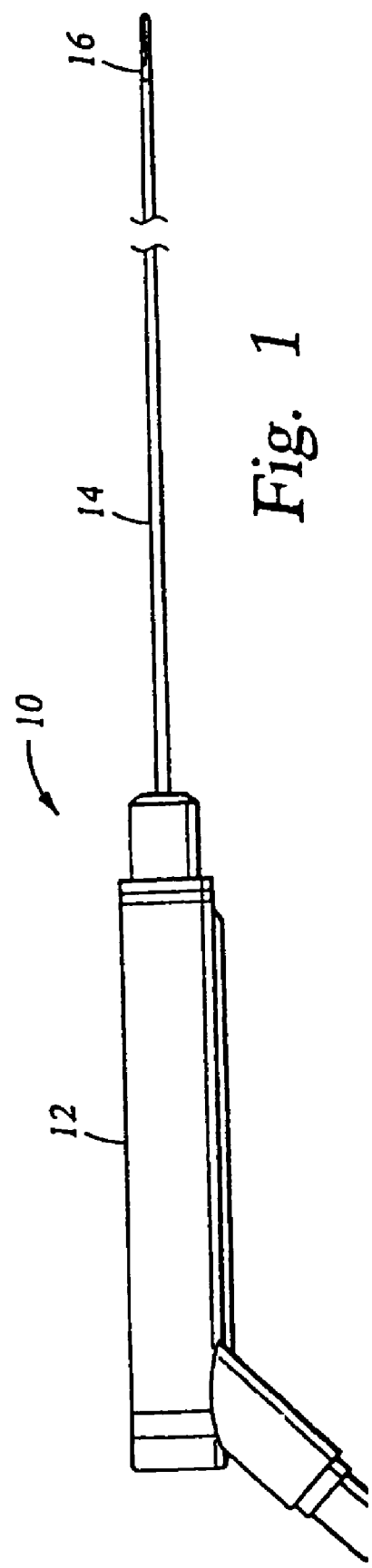
FIG. 1 is a front schematic view of a cryosurgical probe of the type that may be used in accordance with the cooling devices and ethods of the present invention.

Referring now to the Figures, wherein the components are labeled with like numerals throughout the several Figures, and initially to FIG. 1, one configuration of a cryosurgical probe 10 that can be used for cryoablation of endometrial tissue in the uterus of a female patient is shown, in accordance with the present invention. The probe 10 generally includes a handle 12, a hollow tubular cannula 14, and a probe tip 16. The handle 12 can be metallic to facilitate effective sealing of the components to minimize any gas or fluid leakage that might otherwise occur. The handle 12 can also be provided with insulating properties so that it is comfortable for the user to manipulate, such as may be provided by the inclusion of insulation (e.g., aerogel) in the handle or in the form of a vacuum space within the handle. Several components of the refrigeration system, such as a heat exchanger, can optionally be housed within the handle 12, as will be discussed in further detail below. Other components may also be housed within the handle 12, such as various auxiliary instruments to support items such as temperature sensors, heaters, illumination optics, viewing optics, laser optics, and ultrasonic transducers. A conduit 18 preferably extends from the end of the probe 10 opposite the probe tip 16, which may contain tubing for refrigeration system materials, power cables for any electrical components, fiber optical cables to support illumination, viewing, and laser components, and the like.

The cannula 14 may include within its hollow opening other components of the refrigeration system, such as a high-pressure conduit to transport a high-pressure gas mixture from the handle 12 to the probe tip 16 and a low-pressure conduit to return the expanded gas mixture from the probe tip 16 back to the handle 12. Other components of the refrigeration system, such as a Joule-Thompson expansion element, can be housed within the probe tip 16. When a Joule-Thompson expansion element is used for the cryoablation procedures of the present invention, a probe tip or some element located near the probe tip preferably includes at least one small opening that allows passage of a pressurized gas, such as nitrous oxide or carbon dioxide from an inner channel to a space having a larger volumetric capacity. As the gas expands rapidly, it chills to temperatures that are sufficiently low to perform low-temperature surgical techniques. In cases where material flowing through the cannula 14 is at a low temperature, the cannula 14 is preferably designed to minimize heat transfer from the surrounding tissues to the cryogenic gas mixture and to also keep the cannula 14 from unintentionally freezing tissue that comes in contact with its outer surfaces. Thus, the cannula 14 can be formed of a thermally resistive material, such as a rigid plastic, or it can be formed of a metal having insulation provided internally or externally to inhibit heat transfer. The cannula 14 may be a rigid tube or it can be more flexible and shaped differently than shown and/or vary in shape and size along its length.

FIG. 1 illustrates the probe tip 16 as generally including an elongated tube with a rounded tip portion, but it may instead be provided in a number of different forms in accordance with the present invention, as will be discussed in further detail below. As referred to herein, the term "probe tip" is generally intended to refer to the portion of the cryogenic probe device that extends from the end of a cannula that is opposite the fluid supply end of the cannula. Typically, this is the portion of the probe device that performs the actual cryogenic treatment. One exemplary embodiment of a probe tip of the invention generally includes the addition of a balloon with circulating fluid and local cooling through an elongated cannula. In particular, the balloon includes an intermediary heat transfer fluid that distributes cooling from the probe tip to the uterine wall. To use this type of probe tip, the balloon is inserted in its deflated state into the uterus through the cervix. The balloon is then filled with a heat transfer fluid to expand the balloon within the uterine cavity to contact the uterine wall. Preferably, the amount of pressure used is minimized so as to not put unnecessary amounts of pressure on the uterus. Sensors may be provided to measure the temperature and pressure of the fluid within the balloon. Preferably, the internal configuration of the probe tip is designed to maximize the cooling power and lower the temperature of the probe tip during the procedure. In addition, the balloon preferably fully encloses the probe tip. This design may further include a sheath that at least partially covers and contains the balloon in its collapsed position during insertion of the device, after which the sheath can be withdrawn or slid in a direction away from the balloon to thereby release balloon and allow it to expand outwardly to contact the uterine walls. The sheath may further be provided with insulating properties so that it can provide control of the freeze length when it is slid along the length of the extension relative to the balloon.

The balloon embodiment of the probe tip described above may further optionally include insulated lines through which relatively cold fluid can circulate to and from a console that provides the refrigerant. That is, the refrigerant can be cooled to therapeutic temperatures within the console rather than being cooled locally within the uterus. This system consists generally of a hand piece, a balloon, various sensors, fluid lines, and a coupling to the console. A cooler, valves, pumps, and reservoirs may be housed within the console. The console may also have the ability to supply the balloon with warm heat transfer fluid to allow thawing of tissue subsequent to freezing and to allow easier removal of the probe. Thus, the console includes the necessary internal cooler and fluid handling circuitry for it to perform as a generator of warm or chilled heat transfer fluid. The system is preferably also provided with a control system to regulate the flow of heat transfer fluid to and from the balloon and to control the pressure within the balloon. When the temperature of the refrigerant is lowered at a component outside the uterus, it is further preferred that an optionally provided sheath have insulating properties to keep the cooling portion of the tip from ablating the cervical canal when the probe is being inserted through the cervix to the uterus.

Figure 2:
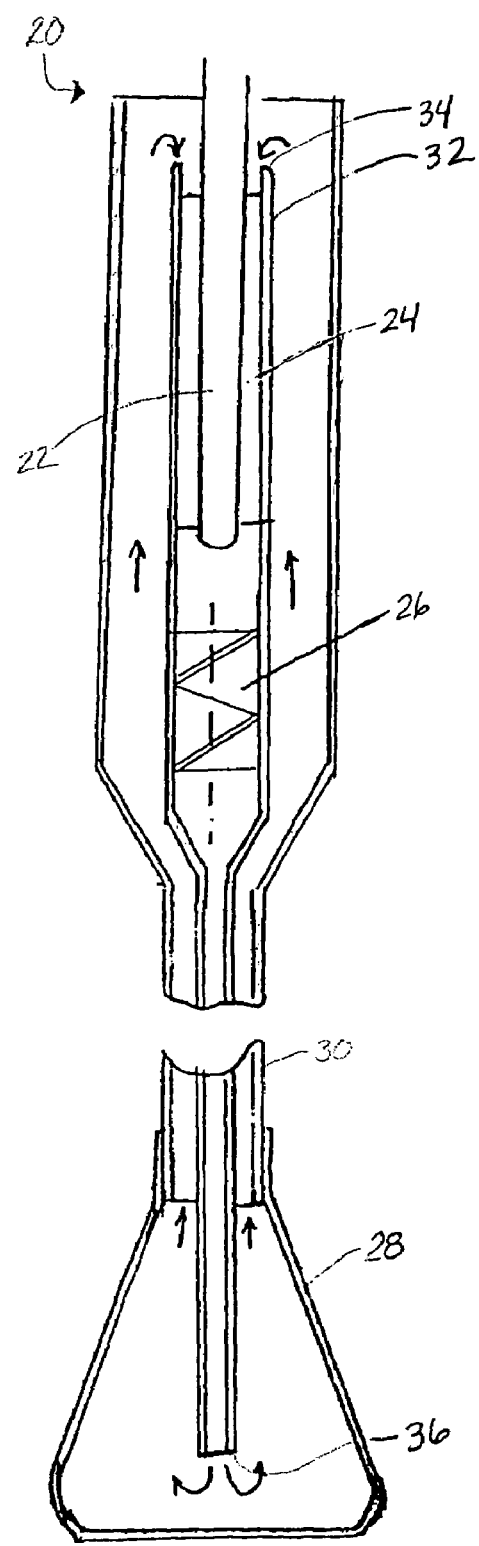
FIG. 2 is a cross-sectional front view of one embodiment of a cannula and probe tip system of a cryosurgical probe, including a heat exchanger that is located at an opposite end of a cannula from a balloon.

One preferred embodiment of a cannula and probe tip system of the type generally described above (i.e., a system including a balloon) is illustrated in FIG. 2, which includes an elongated cannula that is truncated for illustration purposes, with the addition of a balloon at its distal end. The portion of the probe tip shown below the broken line in this embodiment basically represents the end portion of a cannula with a balloon attached to its outer surface, where the distance from the balloon to the handle or control portion of the device can vary widely, depending on the desired configuration of the device. In most cases, the length of the cannula will be considerably longer than the length of the balloon, although it is possible that the cannula is relatively short. In this particular embodiment, a cannula and probe tip system 20 includes a cryoprobe tip 22, a heat exchanger 24, a fluid pump 26, and a balloon 28 attached to the end of a cannula 30. This system is configured so that the cryofluid will be cooled outside the uterus, then transported to the uterine cavity when the balloon is positioned therein. Because the fluid will be extremely cold when transported through the cannula 30, the cannula 30 and other components that carry the cold fluid will preferably be insulated to prevent unintentional freezing of tissues that come in contact with these components. The cannula 30 may be a rigid tubular portion, or may alternatively be made of a flexible material, where the upper portion of the system is then preferably located within a console.

The balloon 28 is shown in this figure in its deployed or partially expanded condition. It is noted that the system 20 may include a moveable sheath (not shown) that extends along at least a portion of the length of the cannula 30. In order to achieve this inflated or partially inflated condition, a volume of fluid is provided to the balloon 28 until it is inflated to the desired size and is at least slightly pressurized. The fluid provided to the balloon 28 may be provided by a portable tank that can provide fluid under pressure, or may be connected to a relatively constant source of fluid that is compressed on site and provided through a supply line.

The system 20 further includes an elongated tube 32 that extends generally from the cryoprobe tip 22, through the cannula 30, and into the balloon 28. The tube 32 has a first end 34 and a second end 36, where the tube 32 is wider at its first end 34 than at its second end 36. In addition, this end 34 is illustrated as being positioned in the handle of the probe, or at some other place spaced at a distance from the balloon. The end 34 is thus positioned near the location within the probe where the fluid within the cryoprobe tip is cooled by Joule-Thompson expansion. At its first end 34, the tube 32 surrounds a portion of the cryoprobe tip 22, which is the area where heat transfer between fluids occurs. The second end 36 of the tube 32 is open to the interior of the balloon 28. In this way, fluid that exits the second end 36 of the tube 32 and enters the balloon 28 will be forced back toward the cryoprobe tip 22 by the pump 26. When the fluid circulates to the first end 34, it is forced back into the space between the cryoprobe tip and the tube 32 and into the area of the heat exchanger 24. That is, the top portion of the cannula 30 closest to the first end 34 is the portion that is included as part of the heat exchanger The heat exchanger 24 includes at least one fin (not visible in this view) that extends from the interior wall of the elongated tube 32 toward the center of the device. The fin or fins help to increase the heat transfer rate of the fluid by increasing the surface area across which convection occurs. The thermal conductivity of the fin material has a strong effect on the temperature distribution along each fin and therefore influences the degree to which the heat transfer rate is enhanced. Thus, any fins that are included in the heat exchanger 24 will preferably be designed and configured to increase the efficiency of changing the temperature of the fluid that is circulated through the balloon, cannula, and other components of the system 20. The fluid within the cryoprobe tip 22 is cooled through Joule-Thompson expansion. The second fluid is cooled in the heat exchanger by the extremely cold temperature of the first fluid in the cryoprobe 22, and then delivered to the balloon 28 by way of the closed loop pumping circuit, as shown. This heat exchange process will thereby cool the second fluid to a predetermined temperature necessary for cryoablation.

Figure 4:
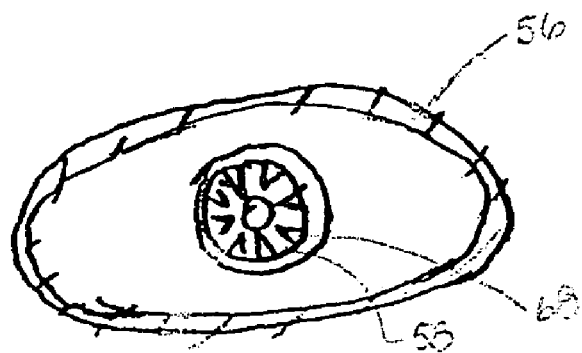
FIG. 4 is a cross-sectional view taken along section line A-A of FIG. 3.
Figure 3:
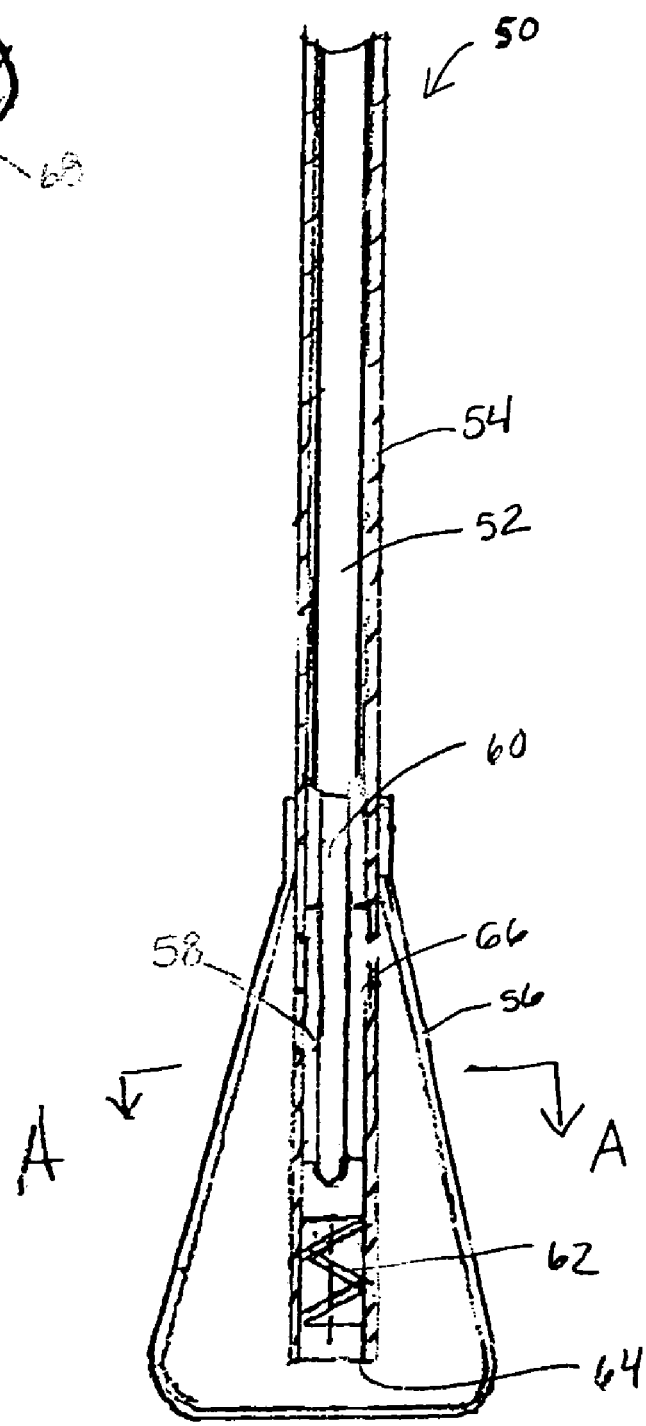
FIG. 3 is a cross-sectional front view of another embodiment of a cannula and probe tip system of the present invention, including a heat exchanger that is located within a cryosurgical balloon.

FIGS. 3 and 4 illustrate another embodiment of a cryosurgical probe tip and balloon system 50 that generally includes an elongated cannula 52 having a sheath 54 that extends along at least a portion of the length of the cannula 52, and a balloon 56 attached at one end of the cannula 52. In this embodiment, the fluid is cooled within the balloon itself, so there is no need to transport the extremely cold fluid through an elongated cannula to the uterine cavity. One preferred method of performing cryoablation in accordance with the invention includes inflating the balloon 56 with a fluid that is relatively warm until it is contacting all of the uterine surfaces that need to be ablated. The balloon 56 is preferably at least slightly pressurized at this point. The warm fluid within the balloon 56 is then replaced with cold fluid through the use of a heat exchanger 58, as described below. Once the fluid reaches its low cryoablation temperature, the endometrium is frozen to the desired thickness. The cold fluid is then replaced with warm fluid, which can again be accomplished through the use of the heat exchanger 58, until the balloon 56 is sufficiently de-iced to allow it to break free of the frozen tissue. The balloon 56 can then be allowed to collapse and optionally be compressed again within a sheath for removal of the probe from the patient.

The system 50 preferably includes a heat exchanger 58 that operates with the use of a primary refrigeration circuit containing a first fluid and a secondary refrigeration circuit containing a second fluid, where both fluids simultaneously circulate through the heat exchanger to change the temperature of the fluids until a desired temperature of one or both fluids is achieved. The first fluid is provided through the cannula to a cryoprobe tip 60 where it is cooled through Joule-Thompson expansion. The second fluid is provided as a warm fluid to the balloon through a separate fluid path. In this case, the heat exchanger is preferably at least small enough to fit through the cervical canal, along with the balloon, cannula, and any other attached components. Because the cooling of the fluid within the balloon occurs more directly when the heat exchanger is located within the balloon, the cooling process can be comparatively quicker and can require less insulation of the other components of the device.

The heat exchanger 58 is also illustrated in FIG. 4, which better illustrates multiple fins 68 extending from the interior wall of the elongated tube toward the center of the device. The fins 68 help to increase the heat transfer rate of the fluid by increasing the surface area across which convection occurs. Thus, any fins 68 that are included in the heat exchanger 58 will preferably increase the efficiency of changing the temperature of the fluid that is circulated through the balloon, cannula, and other components of the system 50. The fins 68 that are used in the heat exchangers of the present invention may have a wide variety of shapes, sizes, and configurations. For example, as shown in FIG. 4, the heat exchanger has eight fins 68 that are generally triangular in shape when viewed from the top. At least a slight gap is provided between each of the fins 68 so that the fluid flow through the device is not substantially obstructed.

A wide variety of designs and configurations are contemplated for the fins used in the heat exchanger of the present invention; however, some operating features should preferably be considered in the selection of a particular fin design to provide an efficient heat exchanger that does not detrimentally impact the operation of the cryosurgical device. One consideration is that there should be sufficient gaps or spaces between adjacent fins so that the pressure drop across the fins is not undesirably high. That is, it is preferable that the same fluids can be used with the heat exchangers of the present invention that include fins as with known systems that do not include fins. Thus, the number, size, shape, and placement of the fins within the heat exchanger should all be considered in determining a configuration that maximizes the heat transfer gained by the fins (i.e., maximizing the surface area across which convection can occur), while not providing a detrimental obstruction of the fluid flow. Further, the effectiveness of the fin design should be calculated to determine whether the fins will provide the desired effectiveness, which is defined as the ratio of the fin heat transfer rate to the heat transfer rate that would exist without the fins. In many cases, the use of many thin, closely spaced fins will provide for more effective heat transfer than wide fins that are spaced further from each other. In addition, the materials from which the heat exchanger and fins are made preferably have a high thermal conductivity to increase the fin effectiveness.

FIG. 6 illustrates a top view of another exemplary design of a heat exchanger 90 of the invention. The heat exchanger 90 includes a plurality of extending fins 92 spaced apart from each other in a spoke-like arrangement around the periphery of the heat exchanger by an equal number of generally rectangular troughs or gaps 94. Again, the size and spacing of the fins 92 and troughs 94 can vary from the illustration, such as by changing the number and size of the fins 92 and the number and size of the corresponding troughs 94. The fins 92 preferably extend along the entire length of the heat exchanger 90, although it is possible that the fins are discontinuous along the heat exchanger length. For one example, the heat exchanger 90 has twelve fins 92, where each fin is oriented at an angle of 30 degrees from each adjacent fin. It is also understood that the fins do not necessarily need to be evenly spaced around the periphery of the heat exchanger.

Figure 8:
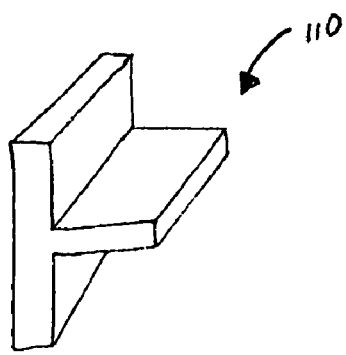
FIGS. 8-10 are perspective views of three exemplary heat exchanger fin configurations of the present invention.
Figure 9:
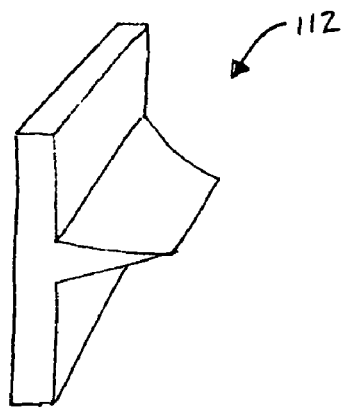
Figure 10:
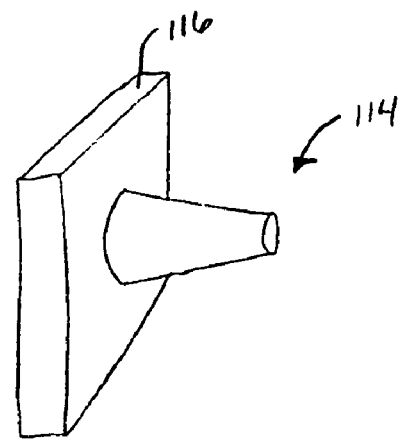

FIG. 7 illustrates a top view of another exemplary design of a heat exchanger 100 that includes a plurality of extending fins 102 spaced apart from each other by an equal number of gaps or troughs 104 in a similar arrangement to that illustrated in FIG. 6. In this embodiment, however, the troughs 104 are rounded at the base of the fins 102, which provides for at least a slightly different flow pattern than if the troughs were squared off. FIGS. 8, 9, and 10 are perspective views of three alternative designs of fins that can be used in a heat exchanger of the invention. In particular, FIG. 8 illustrates a straight fin 110 of uniform cross-section and FIG. 9 shows a straight fin 112 that tapers from its base to its tip (i.e., a nonuniform cross-section), both of which can extend along the length of the heat exchanger in a continuous manner, if desired. The fin 114 of FIG. 10, however, extends in a pin or spike type of manner from a base portion 116 and thus cannot extend continuously along the length of the heat exchanger. Rather, a plurality of these types of fins 114 could be used along the length of the heat exchanger to gain the desired cooling effect.

A cross-sectional side view of an exemplary heat exchanger 80 is shown in FIG. 5, which illustrates a plurality of fins 82 that extend continuously along the entire length of the heat exchanger 80. However, the fins may instead be discontinuous along the length of the heat exchanger, thereby creating additional flow paths for the fluid as it moves through the heat exchanger and past the fins. Alternatively, some of the fins may be continuous while others are discontinuous within a single heat exchanger.

While the description of the heat exchanger with fins or extensions is described above relative to a system including a balloon for cryoablation, it is possible that the heat exchanger of the invention be used for other probe tip configurations that include circulation of fluid through a heat exchanger. Several examples of such probe tip configurations are described in the copending U.S. patent application of the present Assignee filed on even date herewith, having U.S. Ser. No. 11/020,791, entitled "CRYOSURGICAL DEVICES AND METHODS FOR ENDOMETRIAL ABLATION," which is incorporated herein by reference in its entirety. One such example of a probe tip is a multiple-fingered extension that extends from the cooling portion of the probe. The extension includes two or more distinct flexible elongated members that extend from the cooling portion of the probe. The extension may have a corresponding number of internal refrigerant flow tubes or passages, each with its own refrigerant flow. The fingers can each include a capillary tube extending from the end of an inner supply tube toward the ends of the fingers. The capillary tubes can carry refrigerant that is provided by the supply tube at an acceptable treatment temperature for performing the ablation procedure. With any of these multi-fingered probe extensions, a recuperative heat exchanger is preferably used for a primary refrigeration circuit to cool the fingers for the ablation process. This heat exchanger may be located within the control handle, or at some location between the control and refrigerant supply console and the system handle. Alternatively, the heat exchanger may be located within the cool tip portion of the probe. Thus, heat exchangers having internal fins, as described above, can be used with these embodiments to improve the efficiency of those systems.

Another example of a probe tip configuration that can utilize the finned heat exchangers of the present invention is illustrated in FIG. 11. This figure illustrates a system 120 having the basic components of the Her Option Cryoablation System available from American Medical Systems, additionally including a finned heat exchanger 122. FIG. 12 shows an enlarged view of the heat exchanger 122 of FIG. 11, which includes a plurality of fins 124 that extend along the length of the heat exchanger 122 in the direction of its longitudinal axis. It is preferable that the heat exchanger 122 be designed and configured to improve the cooling power of the system by about 60-70 percent as compared to a system that does not include fins. This heat exchanger 122 can include any of the features and configurations of the heat exchanger and fins described herein relative to other systems that include a finned heat exchanger.

The heat transfer fluids used in accordance with the present invention may include a variety of fluids that can provide the necessary cooling and heating of the tip of the device. The fluid is preferably biocompatible so that any unintentional fluid leaks would not be dangerous to the patient. Exemplary fluids include a hydrofluorocarbon fluid, such as Dupont Vertrel XF, which is commercially available from DuPont Fluorochemicals of Wilmington, Del.; a 1-mehosyheptafluoropropane, such as Novec HFE-7000, which is commercially available from the 3M Company of St. Paul, Minn.; a perflurocarbon or perfluorohexane, such as F2 Chemicals Flutec T14 (PF-I-hexane) or PP1 (PF-n-hexane) or combination, which is commercially available from F2 Chemicals Ltd. of the United Kingdom; ethyl alcohol (ethanol) (e.g., alcohol denatured with IPA and MeOH), which is commercially available from Spectrum Laboratory Products Inc. of Gardena, Calif.; a dimethyl polysiloxane, such as Dow Chemicals Syltherm XLT, which is commercially available from the Dow Chemical Company of Midland, Mich.; an aromatic hydrocarbon, such as Dynelene MV, which is commercially available from Dynalene Heat Transfer Fluids of Whitehall, Pa.; and propylene glycol, which is commercially available from Mallinckrodt Baker, Inc., of Phillipsburg, N.J. With these types of heat transfer fluids, the balloon or device in which the fluid is held is preferably made from either a polyurethane or silicone material.

In one particularly preferred embodiment, hydrochlorofluorocarbons (HCFC's), such as Asahiklin AK-225 or AK-225 g (hereinafter referred to as "AK-225"), which are commercially available from the Asahi Glass Co., Ltd. (Chemicals Americas, Inc.), of Tokyo, Japan, can be used as the heat transfer fluid, such as the fluid used to inflate the balloon. In this case, the balloon or device in which the fluid is held is preferably made from a polyurethane material, but may be made from other materials that can stretch to conform to the shape of the cavity in which it is inserted when filled with pressurized fluid, such as silicone, urethane, PET, and the like. The balloon should also have lubricous surface properties which prevent the balloon from sticking to itself and also allow it to easily slide over the uterine wall to allow uniform contact with the endometrium when inflated. Preferably, the balloon material should be relatively thin to minimize the thermal conduction losses due to heat transfer that can occur with balloons having a relatively large thickness, such as greater than about 0.05 mm for example. In addition, the balloon material should not crack or otherwise degrade when subjected to the extremely cold temperatures required for the cryoablation procedure and the balloon material should be compatible with the heat transfer fluid.

However, it is understood that fluids having similar properties to that of AK-225 may also be used as the heat transfer fluid, such as a fluid having a low vapor pressure at room temperature, a fluid having a freezing point that is preferably lower than about −110 degrees C. and a boiling point that is greater than about 50 degrees C., and more preferably has a freezing point that is lower than about −130 degrees C. and a boiling point that is greater than about 60 degrees C. In any case, it is preferred that the boiling point be at least above room temperature so that the fluid remains a fluid and does not vaporize when subjected to temperatures near room temperature. The heat transfer material preferably also has a relatively low viscosity over the entire operating temperature range to avoid large pressure drops, particularly when the material is exiting the balloon as this may generate uncomfortably high pressure within the uterus. The fluid is also preferably chemically inert to prevent degradation of the balloon, fluid lines, valves, seals, and other system components. In order to allow electrical isolation of the patient from the ground, the fluid is preferably not conductive. Further the heat transfer fluid is preferably chemically stable to allow storage for long periods and sterilization if necessary by methods of heat and gamma irradiation, for example. It is also preferably not flammable, not at risk of degrading into flammable or toxic compounds if exposed to electricity or high temperatures, and is both biocompatible and environmentally friendly.

Fluids used in the balloon, such as AK-225, are particular advantageous in accordance with the devices and methods of the present invention because it can remain in its liquid state when subjected to the operating conditions of the system. That is, the fluid preferably remains a liquid even at extremely low temperatures to provide better heat transfer to the patient. This type of fluid is able to cause a desired range of about 5 mm to about 7 mm of ablated tissue thickness to reach a temperature of about −20 degrees C. (which is well above its freezing point) at its outside edge, which is sufficient for ablation under many circumstances. In addition, the fluid used in the balloon preferably also remains a liquid within the balloon to provide a more uniform transfer of cooling to the tissue in contact with the balloon. It is further desirable that the fluid remains a liquid at room temperature and at the highest operating temperatures inside the system, thereby facilitating low pressure circulation of the fluid, ease of fluid handling and safety from a lack of significantly pressurized components in the fluid circuit.

Any of the embodiments of a probe tip discussed above may optionally include some type of disposable protective barrier or layer that can slip over the portion of the device that will be inserted into the patient. Since the protective layer can be removed and discarded after the procedure is complete, the cleaning and sterilization of the probe tip between procedures can be inimized or eliminated and the tip can be used to perform multiple surgeries. The protective layer is preferably provided to be as thin as possible in order to not interfere with the cooling of the tissue that is to be ablated, but thick enough that it does not tear during the insertion of the probe into the patient or during the ablation process. In cases where the probe tip includes multiple fingers or extensions, the protective layer may include individual tips for each of the multiple fingers, or may include a single protective layer or cover that covers all of the multiple fingers. The same or similar materials and designs as the balloons described above can also be used for the disposable protective barriers of the probe tip, if desired.

The probe tips described above and the devices to which they are attached can be designed and manufactured as a permanent part of the device such that once the device can no longer perform the desired surgical procedure, the entire device will be discarded. This may involve few or many uses of the equipment, depending on the device and the operating conditions in which it is used. For example, the use of protective covers can extend the life of the equipment. However, it is contemplated in accordance with the present invention that the probe tips used with a particular device instead be removable and replaceable in a "modular" type of system that allows the breaking of the refrigerant circuit to accept multiple probe tips of the same or different types. In this case, the probe tips could be disposable, thereby eliminating the need to sterilize the devices after each use. A modular system of this type preferably includes valving and storage reservoirs used to recover the refrigerant from the probe tip prior to detachment and evacuation of the probe tip after attachment.

For one example, the modular system includes a gas mix compressor that is used to transfer refrigerant from the probe tip to a storage reservoir during the detachment of the probe tip. The probe tip is then isolated with valves and residual gas in the probe can be vented to the atmosphere. A vacuum pump can then be used to evacuate the air in the system before reattaching the same or a different probe tip. Refrigerant can then be reintroduced to the probe tip by opening or activating the valves that were used to isolate the probe tip during its detachment from the system.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. A cryoablation system for performing endometrial ablation, comprising:
   an elongated tubular cannula having a proximal end, a distal end, a longitudinal axis, an internal fluid path, and a central longitudinal axis;
   a probe tip at the distal end of the cannula;
   a probe handle extending from the proximal end of the cannula;
   a heat exchanger comprising a tubular wall having an inner surface, an outer surface, and a plurality of extensions within the fluid path, wherein the plurality of extensions extend from the inner surface of the tubular wall toward the central longitudinal axis of the cannula; and
   a source of compressed refrigerant fluidly connected to the probe handle.

2. The cryoablation system of claim 1, wherein the probe tip comprises an expandable member.

3. The cryoablation system of claim 1, wherein the each of the plurality of extensions is spaced from each adjacent extension by a gap distance.

4. The cryoablation system of claim 3, wherein the gap distance is identical between each of the plurality of extensions.

5. The cryoablation system of claim 1, wherein the plurality of extensions are continuous along the length of the heat exchanger.

6. The cryoablation system of claim 1, wherein the plurality of extensions are discontinuous along the length of the heat exchanger.

7. A cryoablation system for performing endometrial ablation, comprising:
   an elongated tubular cannula having a proximal end, a distal end, and a longitudinal axis;
   an expandable balloon extending from the distal end of the cannula and fluidly connected to a source of heat transfer fluid by at least one fluid path;
   a pump for circulating the heat transfer fluid into and out of the balloon;

a probe handle coupled to the proximal end of the cannula and in fluidic communication with the balloon through the cannula; and a heat exchanger for varying the temperature of the heat transfer fluid, wherein the heat exchanger is fluidly connected to a secondary refrigerant source, and wherein the heat exchanger comprises a central longitudinal axis, a tubular wall an inner surface, an outer surface, and a plurality of fins extending from the inner surface of the tubular wall toward the central longitudinal axis of the heat exchanger.

8. The cryoablation system of claim 7, wherein the heat exchanger is positioned within the probe handle so that the secondary refrigerant can cool the heat transfer fluid to a treatment temperature before the heat transfer fluid is provided to the balloon.

9. The cryoablation system of claim 7, wherein the heat exchanger is positioned within the cannula so that the secondary refrigerant can cool the heat transfer fluid to a treatment temperature before the heat transfer fluid is provided to the balloon.

10. The cryoablation system of claim 7, wherein the heat exchanger is positioned within a console of the system so that the secondary refrigerant can cool the heat transfer fluid to a treatment temperature before the fluid is provided to the probe handle.

11. The cryoablation system of claim 7, wherein the each of the plurality of extensions is spaced from each adjacent extension by a gap distance.

12. The cryoablation system of claim 11, wherein the gap distance is identical between each of the plurality of extensions.

13. The cryoablation system of claim 7, wherein the plurality of extensions are continuous along the length of the heat exchanger.

14. The cryoablation system of claim 7, wherein the plurality of extensions are discontinuous along the length of the heat exchanger.

* * * * *

UNITED STATES PATENT AND TRADEMARK OFFICE
CERTIFICATE OF CORRECTION

PATENT NO. : 7,381,208 B2 Page 1 of 1
APPLICATION NO. : 11/020792
DATED : June 3, 2008
INVENTOR(S) : Nicholas R. van der Walt et al.

It is certified that error appears in the above-identified patent and that said Letters Patent is hereby corrected as shown below:

Title Page; item (56); page 2, col. 1;
In References Cited, "6,182,666 B1 2/2001 Dobak" should be --6,182,666 B1 2/2001 Dobak,III--.
Column 1, line 35, "anipulating" should be --manipulating--.
Column 11, line 40, "inimized" should be --minimized--.

Signed and Sealed this

Nineteenth Day of August, 2008

JON W. DUDAS
*Director of the United States Patent and Trademark Office*